United States Patent [19]

Collins, Jr.

[11] Patent Number: 4,886,065

[45] Date of Patent: Dec. 12, 1989

[54] IN VIVO ELECTRODE IMPLANTING SYSTEM

[75] Inventor: Earl R. Collins, Jr., La Canada, Calif.

[73] Assignee: California Institute of Technology, Pasadena, Calif.

[21] Appl. No.: 229,284

[22] Filed: Aug. 8, 1988

[51] Int. Cl.[4] .......................... A61B 5/04; A61N 1/05
[52] U.S. Cl. ..................................... 128/642; 128/785
[58] Field of Search ........................ 128/642, 784–786, 128/419 P

[56] References Cited

U.S. PATENT DOCUMENTS 4,282,886  8/1981  King ................................... 128/785
4,402,323  9/1983  White ............................. 128/785 X
4,407,303  10/1983  Akerstrom ......................... 128/785

FOREIGN PATENT DOCUMENTS 2525110  10/1983  France .............................. 128/785

*Primary Examiner*—Lee S. Cohen
*Attorney, Agent, or Firm*—Freilich, Hornbaker, Rosen & Fernandez

[57] ABSTRACT

A cylindrical intramuscular implantable electrode is provided with a strip of fabric secured around it. The fabric is woven from a polyester fiber having loops of the fiber protruding. The end of the main cylindrical body is provided with a blunt conductive nose, and the opposite end is provided with a smaller diameter rear section with an annular groove to receive tips of fingers extending from a release tube. The fingers are formed to spring outwardly and move the fingertips out of the annular groove in order to release the electrode from the release tube when a sheath over the electrode is drawn back sufficiently. The sheath compresses the fingers of the release tube and the fabric loops until it is drawn back. Muscle tissue grows into the loops to secure the electrode in place after the sheath is drawn back. The entire assembly of electrode, release tube and sheath can be inserted into the patient's muscle to the desired position through a hypodermic needle. The release tube may be used to manipulate the electrode in the patient's muscle to an optimum position before the electrode is released.

4 Claims, 2 Drawing Sheets

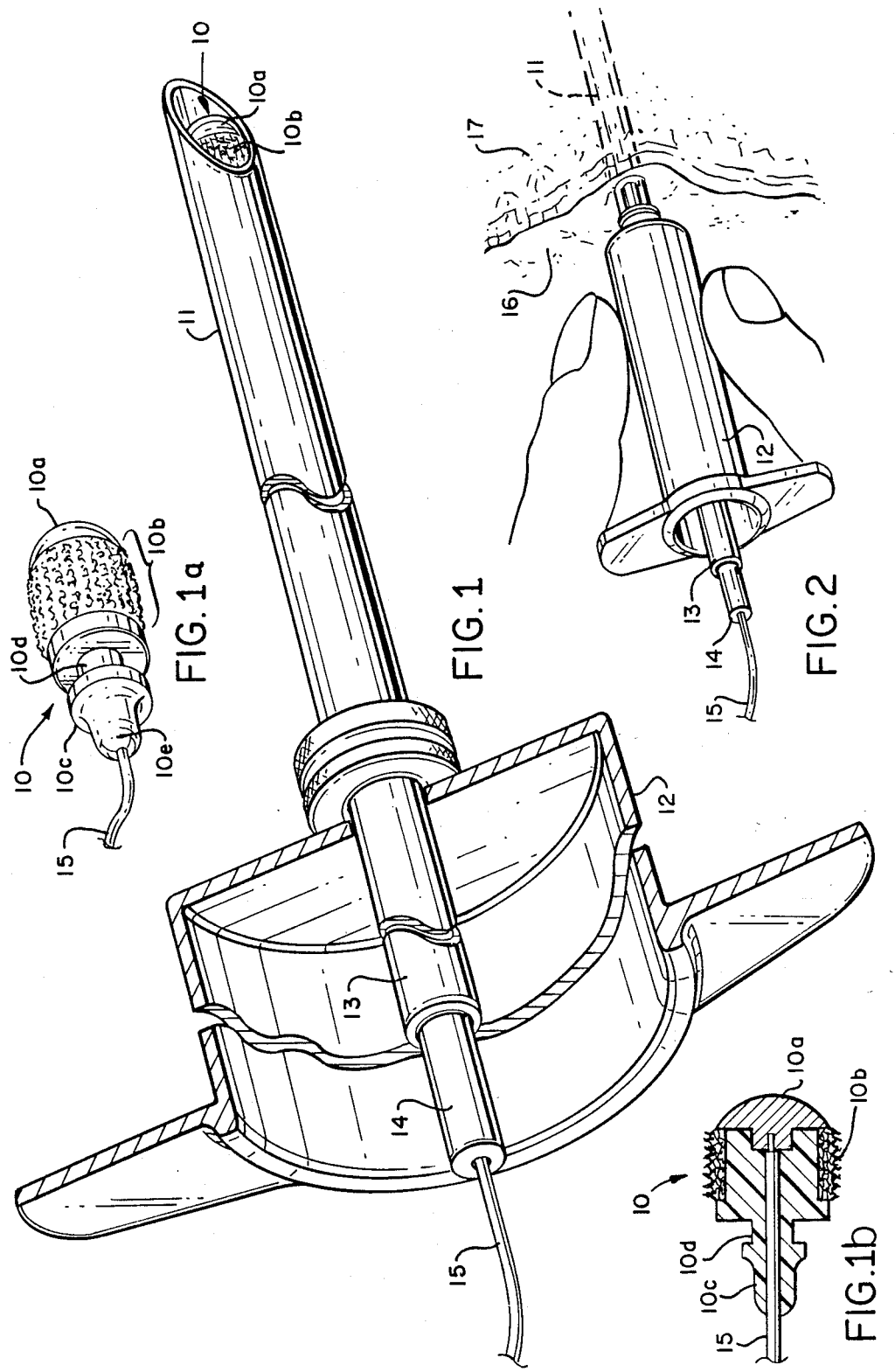

IN VIVO ELECTRODE IMPLANTING SYSTEM

ORIGIN OF THE INVENTION

The invention described herein was made in the performance of work under a NASA contract, and is subject to the provisions of Public Law 96-517 (35 USC 202) in which the Contractor has elected to retain title.

BACKGROUND OF THE INVENTION

This invention relates to an electrode, and to a system for intramuscular implanting the electrode, such as in a vital area adjacent to a nerve, and for adjusting the position of the electrode for optimum results in treating or monitoring a patient.

It is often necessary to treat or monitor a patient repeatedly through an electrode over an extended period of time, and where the electrode is to be positioned in a vital area of muscle tissue, it is desirable to quasi-permanently implant the electrode. For example, in research for applications of computer-driven prosthesis, it is important to quasi-permanently implant electrodes in muscle tissue very near or against nerves. That not only obviates the risk of damage to the vital area through repeated reinsertion of the electrode, but also is much less stressful for the patient. The problem is retaining the electrode in an optimum position once it is properly placed. Through activity on the part of the patient, muscle tissue movement may disturb the optimal placement of the electrode, which may then require removal and re-implanting the electrode.

SUMMARY OF THE INVENTION

In accordance with the present invention, an electrode having a cylindrical main body is provided with a conductive blunt nose, and an insulated flexible conductor passing through the main body to connect with the nose. The cylindrical main body is wrapped with a strip of fabric made of a polyester fiber with loops of fiber protruding through the interstices of the fabric. The fabric is secured, such as by fusing to the cylindrical main body. The rear of the main body opposite the blunt nose has a short cylindrical section of smaller diameter, and an annular groove at the interface with the main cylindrical body. In practice, only the nose need be made of conductive material; the main cylindrical body and the short cylindrical section may be made of plastic. An insulated flexible conductor passes through the short cylindrical section and the main body into electrical contact with the nose. A release tube with gripping fingers protruding longitudinally from the end is placed over the insulated conductor and held by a sheath with the tips of the fingers in the annular groove at the rear of the main cylinder. These fingers are so formed in an arc that they spring out and force the fingertips clear of the annular groove. The fingertips are normally forced inwardly into the annular groove by a sheath placed over the release tube. The sheath also compresses the loops in the fabric against the main cylinder until it is in a proper intramuscular position.

The electrode assembled as just described is inserted into the patient's muscle through a hypodermic needle having an internal diameter slightly larger than the outside diameter of the sheath. Once the electrode assembly is inserted through the needle to very near the proper position, such as for treating or monitoring a nerve, the sheath and release tube assembly is pushed forward in the hypodermic needle channel to fully expose the nose while it is optimally positioned. The hypodermic needle is then withdrawn from the patient leaving the sheath and release tube assembly holding the electrode in place.

Once optimally positioned, the sheath is partially withdrawn to expose all of the fabric to muscle tissue. The compressed loops expand into the surrounding tissue to hold it in position. The electrode is rigidly held at the end of the sheath. During a period of several days, while the tissue is healing and growing into the fabric, the electrode may move slightly out of position, a condition detachable by electronic monitoring. To correct the position of the electrode, it may be moved slightly by means of the rigid sheath and release tube assembly. Once tissue has grown into the electrode loop, the electrode may be released from the sheath and release tube assembly. To accomplish that, the sheath is drawn back sufficiently to allow the gripping fingertips to spring out away from the annular channel of the electrode. Once the electrode is thus released, the release tube is drawn back into the sheath and both are withdrawn from the patient. The insulated conductor is momentarily disconnected (if not still unconnected) from any external equipment that will use the electrode while the release tube and sheath are removed from the patient.

To extract the electrode from the muscle tissue, the procedure is reversed after first threading a hypodermic needle, sheath and retaining tube on the flexible conductor, and then gently inserting the hypodermic needle along the axis of the insulated conductor while maintaining slight tension on the conductor, thus forcing the electrode back into the sheath. This procedure for implanting and removing an electrode obviates the need for any incision in the muscle tissue beyond that made by the tip of the hypodermic needle.

The novel features that are considered characteristic of this invention are set forth with particularity in the appended claims. The invention will best be understood from the following description when read in connection with the accompanying drawings.

BRIEF DESCRIPTION OF THE DRAWINGS

FIG. 1 illustrates an isometric view of an electrode assembly inserted through a hypodermic needle attached to a syringe (partly broken away) for intramuscular implanting in a patient, and FIG. 1a illustrates in an isometric view the electrode itself, and FIG. 1b illustrates a longitudinal cross section the electrode.

FIG. 2 illustrates the hypodermic needle of FIG. 1 with a syringe attached to the threaded rear end of the needle being adjusted in intramuscular position in a patient.

DESCRIPTION OF PREFERRED EMBODIMENTS

Figure 3:
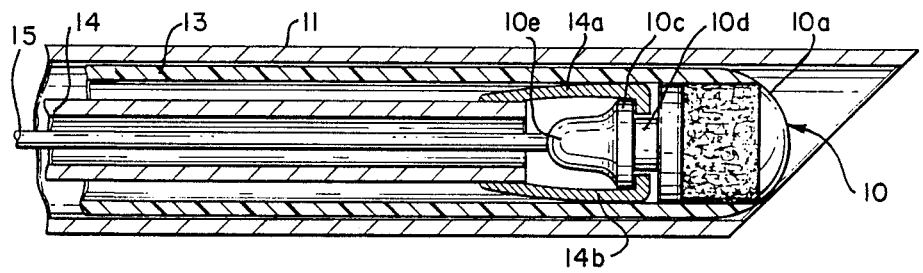
FIGS. 3 through 6 illustrate progressive stages or steps in the process of extracting a sheath and release tube assembly of the electrode assembly in FIG. 1, and in the final stages extracting the hypodermic needle with the assembly if desired.

Referring to FIG. 1, an electrode 10 is shown inserted into a hypodermic needle 11 that is threaded to the end of a syring 12. The plunger of the hypodermic syringe has been removed in order to insert a sheath 13 (which holds the electrode at its tip) into the needle. Inside the sheath is a release tube 14 through which a flexible insulated conductor 15 of the electrode 10 is passed for connection to an instrument (not shown).

The electrode 10 is shown by itself in FIG. 1a as having a blunt nose 10a and a main body 10b covered with a normal synthetic fabric woven from a polyester fiber, such as Dacron, with loops protruding through the interstices of the woven fabric. The main body 10b over which the fabric is secured is recessed slightly (about the thickness of the fabric itself) so that only the loops protruding from interstices of the fabric stand out beyond the larger outside diameter of the electrode as shown in FIG. 1b. These loops, like the loops of a Velcro fastener, should be flexible but still rather stiff, and not soft like cotton terries (uncut loops that form the pile of fabric such as used for bath towels). The rather stiff loops retain the electrode in place in the muscle tissue, and with a few days time the electrode will become more secure as damaged muscle tissue begins to grow in and around the loops during the healing process. The electrode thus becomes quasi-implanted to permit the muscle to be more active without disturbing the placement of the electrode.

Behind the main body 10b of the electrode is a smaller diameter section 10c with an annular groove 10d of the interface with the main body. Note that the main body 10b, rear section 10c and annular groove 10d are formed as one unitary plastic (nonconductive) body, while the nose 10a is made of metal (preferably plated with gold or some alloy of gold, such as Au/Cr) and secured to the main body with the insulated conductor 15 electrically attached.

The annular groove is intended to receive the tips 14c and 14d of gripping fingers 14a and 14b on the end of release tube 14, as shown in FIG. 3. With the sheath 13 over the fingers 14a and 14b, the electrode is gripped so that it may be moved forward and back by moving the release tube 14 relative to the sheath, and relative to the needle 10.

The syringe 12 serves as a handle for inserting the hypodermic needle 11 through the skin 16 and into the muscle 17 of a patient to a position very near a point to be monitored or treated. While holding the syringe steady, as shown in FIG. 2, the electrode 10 at the end of the sheath 13 and release tube 14 is inserted into the needle and pushed forward to where the blunt nose 10a of the electrode 10 is just emerging from the diagonally cut hypodermic needle as shown in FIG. 1, and shown with greater detail in a longitudinal cross section of the assembly in FIG. 3.

The syringe 12 may be removed once the hypodermic needle 11 has been inserted by simply unthreading it from the needle. In that case, the electrode 10 with its sheath and release tube assembly is inserted directly into the hollow needle. If the syringe is not to be removed, and the sheath and release tube assembly is to be inserted into the hollow needle through the syringe, it is preferable to insert it part of the way into the needle before inserting the needle into the patient's muscle. In either case, the flexible conductor 15 may be connected to an instrument during the final stages of positioning the electrode to monitor its interaction with the patient after the hypodermic needle has been withdrawn, thus assuring that it has been optimally positioned by manipulating the sheath and release tube assembly in the needle.

Reference is made throughout to a hypodermic needle, and a syringe, only because they are readily available in various sizes of needle diameter and length, but in practice any hollow needle may be used, and in fact may be designed and fabricated for just this application. Consequently, the terms hypodermic needle and syringe used herein are to be interpreted as being synonymous with the generic terms "hollow needle" and "hollow handle for the needle" which may be threaded together or fabricated as a unitary structure.

Referring now to FIGS. 3 through 6, the first of the series of figures show the electrode 10 in the maximum forward position it should have if inserted into the needle 11 prior to inserting the needle in the muscle of the patient, or the forward position to which it is inserted if it is inserted in the needle after the needle is in the appropriate position in the muscle. After this first insertion step, the needle may be withdrawn from the patient.

Figure 4:
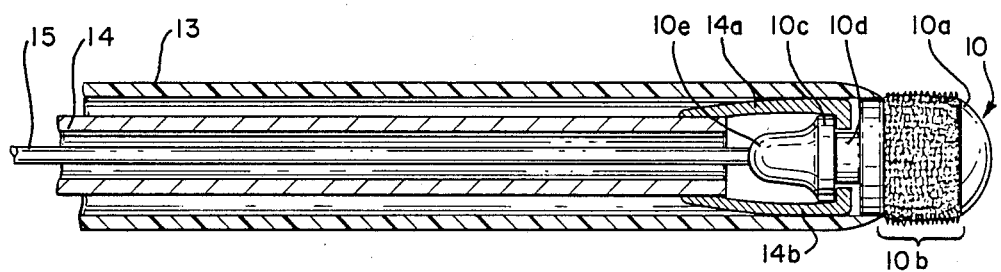

The next step is to advance the electrode slightly, while at the same time retracting the sheath 13 a very slight amount, as shown in FIG. 4, so that the conductive blunt nose 10a will press gently against the muscle tissue or nerve to be monitored or treated. During this step the flexible conductor 15 may be connected to an instrument to assist in determining that the electrode is in an optimum position; if not, the position of the electrode can be adjusted slightly by manipulating the sheath and release tube, both laterally and axially. Note that the sheath is still in position over the fingers 14a and 14b to hold their fingertips 14c and 14d in the annular groove just behind the cylindrical main body 10b. The fabric with loops secured to that cylindrical main body is thus fully exposed to surrounding tissue which will close around and grow into the loops of the fabric, thus securing the electrode in place.

Figure 5:
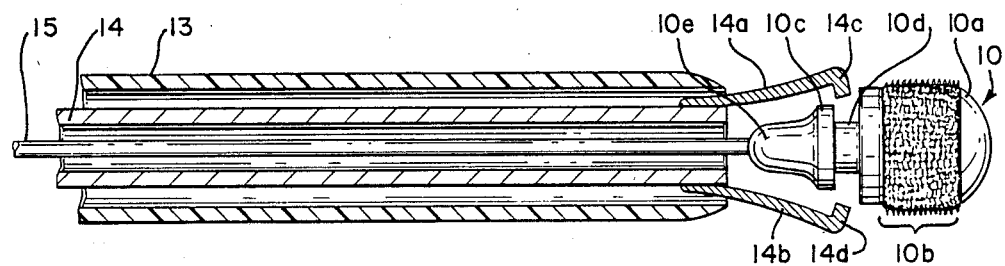

Once the optimum position of electrode is established, the sheath 13 is further extracted, sufficiently to uncover the fingers 14a and 14b, which are biased to spring out when released by the sheath. These fingers are preferably formed in the shape of arcs, either at the time they are produced as an integral part of the release tube 14, or at the time they are separately produced for attachment to the end of the release tube 14 by fusing, brazing or otherwise permanently securing the fingers to the release tube. Consequently, when the sheath is withdrawn far enough relative to the release tube, the fingers spring outwardly, away from the small diameter section of the electrode sufficiently for the fingertips to clear the retaining groove, as shown in FIG. 5.

Figure 6:
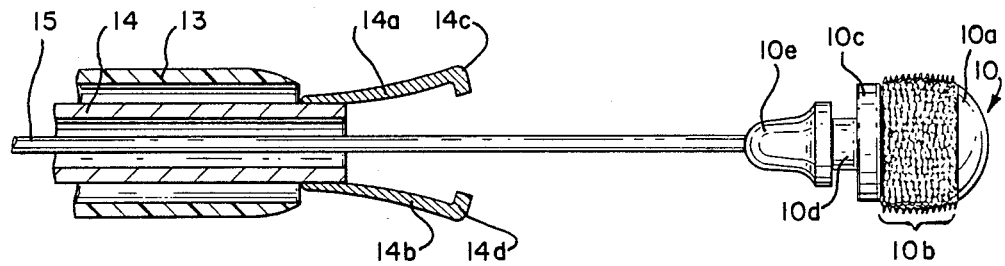

Once the fingertips clear the retaining groove of the electrode, the sheath and retaining tube may be withdrawn in one coordinated movement, as shown in FIG. 6, or in separate movements. At that time, the sheath is peferably moved forwardly sufficiently to cover the fingers so that they do not cause any further tissue damage as they are withdrawn. The loops in the fabric secured around the main cylindrical section of the electrode become "entangled" with tissue which grows to hold the electrode in place. Tissue that has been damaged by the invasion will heal, and as tissue grows in the healing process, the electrode becomes even more securely held in place, even to the point of requiring a subsequent invasion with a hypodermic needle, in the reverse sequence of the steps outlined with reference to FIGS. 3-6 to remove it. The rear section 10e of the electrode is bell shaped to facilitate the fingertips riding up and over the smaller diameter section 10c and into the retaining groove during this reserve removal process. When it is sensed the fingertips are in position over the groove, the sheath is moved forward over the fingertips, thus locking the electrode and release tube together for extraction of the electrode through the hypodermic needle. The flexible conductor 15 serves as a guide while inserting the needle. Thereafter the needle guides the sheath and release tube assembly into engagement with the electrode for removal.

The flexible conductor is preferably made to have high tensil strength such as by providing a stainless steel wire as the core, and plating it with gold, or some alloy of gold, such as Au/Cr, for high conductivity. The nose of the electrode 10a may be made of the same materials, namely stainless steel plated with Au/Cr, and preferably brazed together before plating the nose. The flexible conductor need be only 8 to 10 inches long, and may already be insulated except at the tip that is to be electrically connected to the nose, such as by brazing; if not, an insulating plastic sleeve is placed over the conductor after brazing. The insulated conductor is then inserted through an axial passage in the cylindrical main body 10b, the smaller diameter section 10c, and the rear section 10e, all of which may be formed as a unitary structure, as noted hereinbefore, using a suitable plastic material, such as thermoplastic acetal resin commercially available under the trade name Delrin. This plastic structure may be heated with the nose, conductor and fabric in place sufficiently to just begin to melt. Then upon cooling, the nose, conductor and fabric will fuse together with a strong bond. Alternatively, a plastic resin may be used for bonding.

The hypodermic needle 11 is preferably made of surgical steel to provide a sharp cutting edge, and so it is sectioned as metal in the drawings. The release tube 14 is also preferably made of steel so that it will be sturdy for manipulating the position of the electrode in the muscle tissue. It too is sectioned in the drawings as metal. The sheath 13, however, serves mainly to hold in the fingers with their tips in the annular groove until the release tube is to be extracted. Consequently, the sheath may be plastic, as indicated by hatching in the cross-sectioned drawings, and is preferably plastic to provide insulation between the electrode and needle, and between the electrode and release tube. This insulation is important if the flexible conductor is to be connected to an electronic instrument during the procedure for placing the electrode, and thereafter until the sheath and release tube are removed. A return current path for the electrode is provided at all times by a suitable good connection to the electronic instrument made by a patch somewhere on the patient's skin.

The diameter of the electrode may be virtually any dimension, from less than 2 mm to more than 1 cm, and the length of the electrode would be proportional from less than 5 mm to more than 2.5 cm. As the electrode diameter increases, the difficulty of inserting the hollow needle increases, mainly due to a tendency for the needle to fill with tissue. Consequently, for ease of inserting the needle, the blunt nose electrode should be positioned in the needle as shown in FIG. 3 during the procedure for inserting the needle into the patient's muscle. The blunt nose of the electrode will then tend to deflect tissue away from the channel in the needle, thus avoiding the problems of a clogged needle obstructing insertion of the electrode to the desired position in the patient's muscle.

Although particular embodiments of the invention have been described and illustrated herein, it is recognized that modifications and variations may readily occur to those skilled in the art. Consequently, it is intended that the claims be interpreted to cover such modifications and variations.

What is claimed is:

1. An electrode comprising a body of solid material and a conductive surface exposed on one side of said body of said material, said body being covered with a nonsoluble synthetic fabric and said fabric having loops protruding through interstices of the fabric, a flexible insulated conductor for making an electrical connection through said body to said conductive surface, said body securely holding said insulated conductor in electrical contact with said conductive surface, said body being comprised of a main cylindrical section, and said conductive surface forming a blunt nose for the electrode at one end of said cylindrical section, said insulated conductor passing through said main cylindrical section from the end opposite said blunt nose to said blunt nose for electrical contact therewith, said fabric being secured around said main cylindrical section, and said body being comprised of a smaller diameter section extending from said main cylindrical section on the end thereof opposite said blunt nose, said smaller diameter section having an annular groove formed at the interface with said main cylindrical section, and said insulated conductor passes through both said smaller diameter section and said main cylindrical section along the axis thereof.

2. An electrode as defined in claim 1 wherein said smaller diameter section includes a rear section which tapers from the diameter of said smaller diameter section to the diameter of said insulated conductor, and said insulated conductor passes through said rear section along the axis thereof.

3. A system for implanting an electrode in tissue of a patient comprised of body of solid material and a conductive surface exposed on one side of said body of solid material, said body being covered with a nonsoluble synthetic fabric and said fabric having loops protruding through interstices of the fabric, a flexible insulated conductor for making an electrical connection through said body to said conductive surface, said body securely holding said insulated conductor in electrical contact with said conductive surface, said body being comprised of a main cylindrical section, and said conductive surface forming a blunt nose for the electrode at one end of said cylindrical section, said insulated conductor passing through said main cylindrical section from the end opposite said blunt nose to said blunt nose for electrical contact therewith, said fabric being secured around said main cylindrical section, and said body being comprised of a smaller diameter section extending from said main cylindrical section on the end thereof opposite said blunt nose, said smaller diameter section having an annular groove formed at the interface with said main cylindrical section, and said insulated conductor passes through both said smaller diameter section and said main cylindrical section along the axis thereof, said system including a rigid hollow tube surrounding said insulated conductor of said electrode, said hollow tube having an inside diameter greater than said insulated conductor and an outside diameter less than the diameter of said main cylindrical section of said electrode, said hollow tube having at least two fingers extending from one end thereof, said fingers being formed with fingertips extending radially inward toward the axis of said tube, and the body of said fingers being formed to normally arc out away from the axis of said tube sufficiently for said fingertips to have a space between them of at least the diameter of said smaller diameter section of said electrode, and a sheath surrounding said hollow tube, said sheath having an inside diameter substantially equal to or slightly greater than the diameter of said blunt nose of said electrode for compressing said loops of said fabric around said main cylindrical section of said electrode and forcing said fingers toward each other with their fingertips in said annular groove at the interface of said smaller diameter section with said main cylindrical section while said sheath is positioned around said hollow tube and over said main cylindrical section of said electrode to hold said fingertips in said groove and thus lock said electrode to said hollow tube until said sheath is drawn back over said hollow tube.

4. A system for implanting an electrode in tissue of a patient as defined in claim 3 including a hypodermic needle surrounding said sheath and electrode, said hypodermic needle having an inside diameter sufficiently greater than the outside diameter of said sheath to permit implanting said electrode in said tissue with said sheath and hollow tube passing through said needle, after which said needle may be withdrawn, and to position said electrode in said tissue by manipulating said hollow tube sufficiently, after which said sheath may be drawn back over said hollow tube to release said electrode in order for said sheath and hollow tube to be withdrawn from the patient leaving said electrode secured in place by tissue growth in said loops.

* * * * *